United States Patent [19]

Amano et al.

[11] Patent Number: 5,274,085
[45] Date of Patent: Dec. 28, 1993

[54] PROCESS FOR PREPARING ERYTHROMYCIN A OXIME OR A SALT THEREOF

[75] Inventors: Takehiro Amano, Urawa; Masami Goi, Saitama; Kazuto Sekiuchi, Tatebayashi; Tomomichi Yoshida; Masahiro Hasegawa, both of Omiya, all of Japan

[73] Assignee: Taisho Pharmaceutical Co., Ltd., Japan

[21] Appl. No.: 350,789

[22] Filed: May 12, 1989

[30] Foreign Application Priority Data

May 19, 1988 [JP] Japan ................ 63-122723

[51] Int. Cl.$^5$ ................................. C07H 1/00
[52] U.S. Cl. ..................... 536/7.4; 536/7.2; 536/18.5
[58] Field of Search ............ 536/7.4, 7.2, 18.5

[56] References Cited

U.S. PATENT DOCUMENTS

| 4,349,545 | 9/1982 | Gouin d'Ambrieres et al. | 536/7.4 |
| 4,526,889 | 7/1985 | Bright | 536/7.2 |
| 4,672,109 | 6/1987 | Watanabe et al. | 536/7.2 |

FOREIGN PATENT DOCUMENTS

| 0109253 | 5/1984 | |
| 0158467 | 10/1985 | European Pat. Off. |
| 62-81399 | 4/1987 | Japan ................ 536/7.2 |
| 62-87599 | 4/1987 | Japan ................ 536/7.2 |
| 1100504 | 10/1966 | United Kingdom ........ 536/7.2 |

OTHER PUBLICATIONS

Tetrahedron Letters, No. 2, Jan. 1970, pp. 157-160, Pergamon Press.
R. W. Alder et al.: "Mechanism in Organic Chemistry", 1971, pp. 321-322.
P. Sykes: "A Guidebook to Mechanism in Organic Chemistry", edition 5, 1981, pp. 215-217.
Morrison et al. Organic Chemistry, Third Edition, published by Allyn and Bacon, Inc. (1979) p. 640.

Primary Examiner—Johnnie R. Brown
Assistant Examiner—Elli Peselev
Attorney, Agent, or Firm—Lorusso & Loud

[57] ABSTRACT

A process for preparing erythromycin A oxime or a salt thereof which comprises reacting erythromycin A with hydroxylamine using an acid, is disclosed. Erythromycin A oxime and the salts thereof are useful as intermediates for the synthesis of macrolide antibiotics.

9 Claims, No Drawings

PROCESS FOR PREPARING ERYTHROMYCIN A OXIME OR A SALT THEREOF

BACKGROUND OF THE INVENTION

1. Field of the Invention

The present invention relates to a process for preparing erythromycin A oxime or a salt thereof useful as intermediates for the synthesis of macrolide antibiotics.

2. Description of the Prior Art

Recently, various chemical modifications of natural macrolide antibiotics have been made to develop synthetic macrolide antibiotics having more excellent feature as medicines. Erythromycin A oxime and the salts thereof are important as intermediates of these synthetic macrolide antibiotics.

There are known processes for preparing erythromycin A oxime by reacting erythromycin A with hydroxylamine hydrochloride using various bases such as, for example, barium carbonate (British Patent No. 1,100,504), pyridine (European Patent No. 109,253A), sodium carbonate (Japanese Patent Kokai No. 62-81,399), imidazole (U.S. Pat. No. 4,672,109) and sodium acetate (Japanese Patent Kokai No. 62-87,599).

Also known is a process by which erythromycin A is reacted with hydroxylamine in dry methanol at room temperature to obtain erythromycin A oxime in a moderate yield (Tetrahedron Letters, p. 157, 1970).

Of the above processes, the processes using hydroxylamine hydrochloride as the base have a problem because hydroxylamine hydrochloride is expensive. In addition, the use of an inorganic bases as the base results in formation of a large amount of the inorganic salt, and therefore, troublesome procedures are required for isolation and purification of erythromycin A oxime from the reaction mixture.

On the other hand, the process using free hydroxylamine provides only less than 20% yield of erythromycin A oxime even after reaction for 35 days, so that it is not practical (See Reference Example described below).

SUMMARY OF THE INVENTION

As a result of research to solve the drawbacks of the prior art processes, the present inventors have found a solution to the above problem by reacting erythromycin A with inexpensive hydroxylamine in place of hydroxylamine hydrochloride using an acid in place of the base under given conditions.

An object of the present invention is to provide a process on an industrial scale for preparing erythromycin A oxime or a salt thereof in good yield and good purity by simple procedures.

According to the present invention, erythromycin A oxime or a salt thereof can be prepared by reacting erythromycin A with hydroxylamine using an acid.

DETAILED DESCRIPTION OF THE INVENTION

Hydroxylamine used in the present invention may be an aqueous hydroxylamine solution as well as dry hydroxylamine.

Examples of the acid are organic acids such as formic acid, acetic acid and propionic acid, and inorganic acids such as hydrochloric acid. Accordingly, the salt form products of the present invention are salts of such organic and inorganic acids.

The reaction solvents are preferably alcohols, and more preferably methanol. The reaction temperature may be chosen from room temperature to the reflux temperature of the solvent. The conclusion of the reaction can be recognized by determining the disappearance of erythromycin A using thin layer chromatography or high performance liquid chromatography.

When reacting erythromycin A with hydroxylamine, the addition of the acid increases the rate of formation of erythromycin A oxime. However, when more than a certain amount of the acid is added, an hemiacetal which formed by the reaction of the 9-carbonyl group with the 6-hydroxyl group of erythromycin A is dehydrated to give the corresponding enol-ether form. In order to obtain erythromycin A oxime in good yield, it is necessary to prevent the formation of the enol-ether form. For this reason the relative amounts of hydroxylamine, the acid and the reaction solvent may be as follows. The amount of hydroxylamine is more than 1.5 equivalents, and preferably from 3 to 6 molar equivalents relative to erythromycin A, while more than 6 molar equivalents can give comparable yield to the above. The acid is added in an amount to adjust the pH of the reaction solution from 5.5 to 7.5, and preferably from 6.0 to 7.0. The amount of reaction solvent is preferably from 0.7 to 6 ml, and more preferably from 0.8 to 4 ml relative to 1 g of erythromycin A.

The reaction of erythromycin A with hydroxylamine using an acid under the above conditions precipitates the salt of erythromycin A oxime in the reaction mixture. After completion of the reaction, crystals of the salt of erythromycin A oxime can be collected in good purity only by filtration.

To the salt is added an aqueous ammonia or an aqueous alkali solution (e.g., sodium hydroxide, potassium hydroxide, sodium carbonate, sodium hydrogen carbonate and the like), the mixture is extracted with an organic solvent such as dichloromethane, ethyl acetate and the like, and the extract is concentrated to give erythromycin A oxime easily.

Alternatively, the salt of erythromycin A oxime in the reaction mixture without isolation is mixed with an aqueous ammonia or an aqueous alkali solution as described above, and the mixture is extracted with an organic solvent such as dichloromethane, ethyl acetate and the like, and the extract is concentrated to give the crude crystals, which are then recrystallized to give erythromycin A oxime.

According to the present invention, erythromycin A oxime can be obtained in good yield by using hydroxylamine and an acid by simple procedures. Accordingly, erythromycin A oxime can be prepared inexpensively.

Furthermore, large amounts of the inorganic base and the inorganic salt do not exist in the reaction system of the present invention so that the end product can be easily isolated and purified and the amount of the reaction solvent can be reduced without any hindrance to stirring of the reaction system. Accordingly, a large amount of the end product can be prepared for the scale of the equipment. In addition, since the concentration of the reaction solution rises, the side formation of the enol-ether form which proceeds in an intramolecular reaction can be reduced to give the end product in good purity and good yield.

The present invention will be illustrated in more detail by the following Examples. Erythromycin A used in the Examples and Reference Example was of 90% purity.

EXAMPLE 1

To 6.40 kg of erythromycin A was added 6.00 l of methanol, and the mixture was stirred at 60° C. for an hour. To the suspension was added a mixture of 2.88 kg of 50% aqueous hydroxylamine solution and 1.18 kg of 90% formic acid, and the mixture (pH 6.26) was stirred at 58° C. for 4.5 hours and then at 40° C. overnight. After further stirring at 5° C. for 3 hours, the reaction mixture was filtered by centrifuge to separate the crystals, which were then dried at 60° C. with a forced air dryer for 12 hours to give 5.75 kg of erythromycin A oxime formate, m.p. 156°–158° C.

To 5.75 kg of the salt was added 30 ( of 10% aqueous ammonia, the mixture was extracted with 67 ( of dichloromethane, and the extract was dried over 1.70 kg of anhydrous magnesium sulfate. The dichloromethane was evaporated to give crystals, which were then dried at 60° C. with a forced air dryer for 12 hours to give 5.30 kg of erythromycin A oxime, m.p. 156°–159° C.

EXAMPLE 2

To a suspension of 14.68 g of erythromycin A in a 16.1 ml of methanol was added 6 ml of 50% aqueous hydroxylamine at 56° C., and the mixture was stirred for 30 minutes. Then, the mixture was adjusted to pH 6.30 by adding 4.35 ml of acetic acid at 60° C. over a 20-minute period, and stirred at 60° C. for 5 hours and then at 3° C. for 2 hours. The crystals which formed were collected by filtration, washed with 5 ml of cold methanol and dried to give 13.47 g of erythromycin A oxime acetate, m.p. 152°–154° C.

The salt obtained above was treated in a similar manner to that of Example 1 to separate the crystals, which were then recrystallized from dichloromethane-hexane to give 10.79 g of erythromycin A oxime.

EXAMPLE 3

To a suspension of 14.68 g of erythromycin A in 15 ml of methanol was added at 57° C. a mixture of 4.14 ml of 50% aqueous hydroxylamine solution and 2.31 ml of 12N hydrochloric acid, and the mixture (pH 6.40) was stirred at 60° C. for 8 hours and then at 3° C. for 4 hours. The crystals which formed were collected by filtration, washed with 10 ml of cold methanol and dried to give 9.98 g of erythromycin A oxime hydrochloride, m.p. 189°–192° C.

The salt obtained was treated in a similar manner to that of Example 1 by using 2N aqueous sodium hydroxide solution and dichloromethane to produce a crude crystals, which were then recrystallized from dichloromethane-hexane to give 9.30 g of erythromycin A oxime.

EXAMPLE 4

To a solution of 15.8 g of erythromycin A in 79 ml of dry methanol was added 3.3 g of hydroxylamine, and the solution was adjusted to pH 6.40 (27° C.) by adding 6.7 ml of acetic acid at room temperature. The reaction solution was allowed to stand at room temperature for 6 days, the methanol was evaporated, and the mixture was cooled on ice for 3 hours. The crystals which formed were collected by filtration and dried to give 9.58 g of erythromycin A oxime acetate.

The crystals were treated in a similar manner to that of Example 1 to give 9.27 g of erythromycin A oxime.

Reference Example [Preparation without acid]

To a solution of 15.8 g of erythromycin A in 79 ml of dry methanol was added 3.3 g of hydroxyamine, and the mixture was allowed to stand at room temperature. The reaction rate was calculated by determining the formed erythromycin A oxime and the remaining erythromycin A with lapse of time by means of high performance liquid chromatography.

The conditions of high performance liquid chromatography and the results are as follows.

| <The conditions of high performance liquid chromatography> | |
|---|---|
| Column: | TSK gel, ODS-120A (Toyo Soda) 4.6 mm ID × 25 cm |
| Solvent: | methanol/water (70/30, 0.04% monoethanolamine) |
| Flow rate: | 1.0 ml/min. |
| Temperature: | 65° C. |
| Detection: | UV (220 nm) |

| | <Results> | |
|---|---|---|
| | Peak area (%) | |
| Reaction time | (a) | (b) |
| 2 days | 92.8 | 2.9 |
| 7 days | 89.1 | 6.7 |
| 21 days | 71.6 | 14.3 |
| 35 days | 46.4 | 29.8 |

(note)
(a): erythromycin A
(b): erythromycin A oxime

The molar extinction coefficient of (b) under the conditions was about 5 times as large as that of (a).

It is appearant from the results of the above test that when the process is carried out without using an acid, the yield of erythromycin A oxime obtained by the reaction even for 35 days does not reach to 20%.

What is claimed is:

1. A process for preparing erythromycin A oxime or a salt thereof which comprises:
    admixing erythromycin A, hydroxylamine and an acid to form a reaction admixture, said acid being added in an amount sufficient to adjust said reaction admixture to a pH of 5.5 to 7.5; and
    reacting said erythromycin A with said hydroxylamine in said reaction admixture to form erythromycin A oxime or a salt thereof.

2. The process of claim 1 wherein said hydroxylamine is added in the form of an aqueous solution.

3. A process according to claim 1, wherein the acid is formic acid, acetic, acid, propionic acid or hydrochloric acid.

4. A process according to claim 1, wherein the reaction admixture additionally contains a solvent.

5. A process according to claim 4, wherein the solvent is an alcohol.

6. A process according to claim 5, wherein the alcohol is methanol.

7. A process according to claim 4, wherein the amount of the solvent is from 0.7 to 6 ml per 1 g of erythromycin A.

8. The process of claim 1 wherein said acid is present in an amount providing a pH of 6.0 to 7.0.

9. The process of claim 1 wherein more than 1.5 equivalents of said hydroxylamine are used per equivalent of erythromycin A.

* * * * *

UNITED STATES PATENT AND TRADEMARK OFFICE
CERTIFICATE OF CORRECTION

PATENT NO. : 5,274,085
DATED : December 28, 1993
INVENTOR(S) : Amano, et. al.

It is certified that error appears in the above-indentified patent and that said Letters Patent is hereby corrected as shown below:

Column 3, line 15, delete "30 (" and insert --30ℓ--;
        line 16, delete "67(" and insert --67ℓ--; and
        line 53, delete "a"--.

Signed and Sealed this

Thirtieth Day of August, 1994

Attest:

BRUCE LEHMAN

Attesting Officer      *Commissioner of Patents and Trademarks*